(12) United States Patent
Ruvolo et al.

(10) Patent No.: US 10,017,820 B2
(45) Date of Patent: Jul. 10, 2018

(54) DETECTION OF GENOMIC REARRANGEMENTS BY SEQUENCE CAPTURE

(71) Applicant: Agilent Technologies, Inc., Santa Clara, CA (US)

(72) Inventors: Michael Ruvolo, Santa Clara, CA (US); Emily Marine Leproust, Santa Clara, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 258 days.

(21) Appl. No.: 14/772,064

(22) PCT Filed: Mar. 5, 2013

(86) PCT No.: PCT/US2013/029166
§ 371 (c)(1),
(2) Date: Sep. 1, 2015

(87) PCT Pub. No.: WO2014/137328
PCT Pub. Date: Sep. 12, 2014

(65) Prior Publication Data
US 2016/0017425 A1     Jan. 21, 2016

(51) Int. Cl.
*C12Q 1/68* (2018.01)
*C12Q 1/6883* (2018.01)
*C12Q 1/683* (2018.01)
*C12Q 1/6827* (2018.01)

(52) U.S. Cl.
CPC .......... *C12Q 1/6883* (2013.01); *C12Q 1/683* (2013.01); *C12Q 1/6827* (2013.01)

(58) Field of Classification Search
None
See application file for complete search history.

(56) References Cited

U.S. PATENT DOCUMENTS

| 5,731,153 A | 3/1998 | Lucas et al. |
| 8,034,917 B2 | 10/2011 | Yamada |
| 2009/0239764 A1 | 9/2009 | Sparks et al. |
| 2010/0210469 A1 | 8/2010 | Kang et al. |

FOREIGN PATENT DOCUMENTS

| EP | 1329517 A1 | 7/2003 |
| WO | WO 2005/111236 A1 | 11/2005 |
| WO | WO2012123387 A1 | 9/2012 |

OTHER PUBLICATIONS

Supplementary European Search Report issued for European Application No. 13877007.8, dated Oct. 26, 2016.

*Primary Examiner* — David C Thomas

(57) ABSTRACT

Provided herein is a method of sample analysis. In some embodiments, the method comprises hybridizing fragmented genomic DNA from a test genome with a population of first oligonucleotides of the formula $V_1$-B-$V_2$ in the presence of one or more second oligonucleotides; contacting the product with ligase to join the ends of the fragmented genomic DNA that are hybridized to $V_1$ and $V_2$ to the one or more second oligonucleotides; and subjecting the product to polymerase chain reaction conditions using amplification primers that hybridize to sites that are provided by the one or more second oligonucleotides, wherein production of a product indicates that the test genome contains a chromosomal rearrangement relative to the reference genome.

16 Claims, 5 Drawing Sheets

DETECTION OF GENOMIC REARRANGEMENTS BY SEQUENCE CAPTURE

BACKGROUND

Chromosomal rearrangements, deletions, and other aberrations have long been associated with genetic diseases. Structural abnormalities in chromosomes often arise from errors in homologous recombination. Structural abnormalities can occur in gametes and therefore will be present in all cells of an affected person's body, or they can occur during mitosis and give rise to a genetic mosaic individual who has some normal and some abnormal cells.

There is an ongoing need to develop technical methods for the detection and analysis of chromosomal abnormalities.

SUMMARY

Provided herein is a method of sample analysis, comprising hybridizing fragmented genomic DNA from a test genome with a population of first oligonucleotides of the formula $V_1$-B-$V_2$ in the presence of one or more second oligonucleotides; contacting the product with ligase to join the ends of the fragmented genomic DNA that are hybridized to $V_1$ and $V_2$ to the one or more second oligonucleotides; and subjecting the product to polymerase chain reaction conditions using amplification primers that hybridize to sites that are provided by the one or more second oligonucleotides, wherein production of a product indicates that the test genome contains a chromosomal rearrangement relative to the reference genome.

BRIEF DESCRIPTION OF THE FIGURES

The skilled artisan will understand that the drawings, described below, are for illustration purposes only. The drawings are not intended to limit the scope of the present teachings in any way.

FIG. 1 schematically illustrates two types of halo probe.

FIG. 2 schematically illustrates an exemplary composition of first oligonucleotides used in the subject method.

FIG. 3 schematically illustrates one embodiment of the subject method.

FIG. 4 schematically illustrates one implementation of the subject method.

FIG. 5 schematically illustrates one implementation of the subject method.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale &

Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

Figure 1:
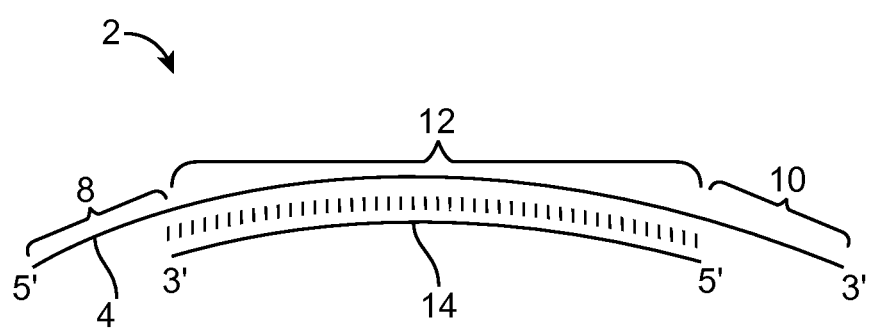
Figure 1:
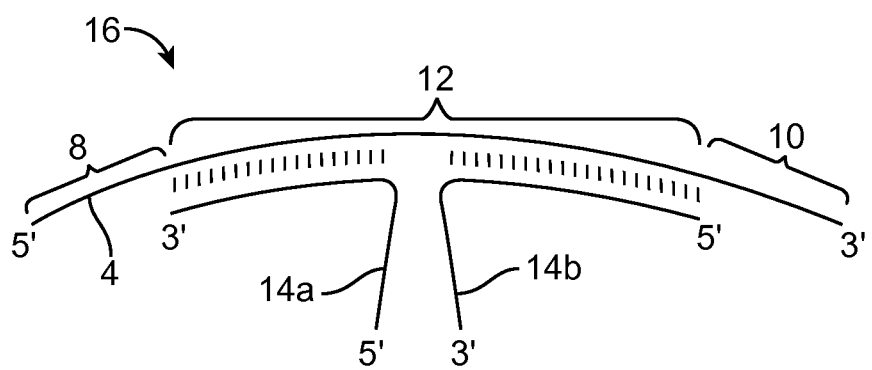

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example. In certain cases, a population of oligonucleotides can be made by fabricating an array of the oligonucleotides using in situ synthesis methods, and cleaving oligonucleotides from the substrate. Examples of such methods are described in, e.g., Cleary et al (Nature Methods 2004 1: 241-248) and LeProust et al (Nucleic Acids Research 2010 38: 2522-2540).

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., at least 5 or 10 times, up to 30 or 40 or more times) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m = 81.5 + 16.6(\log_{10}[Na^+]) + 0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "population" and "collection" are used interchangeably to refer to something that contains at least 2 members. In certain cases, a plurality, population or collection may have at least 10, at least 100, at least 200, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

A "binding site" for an oligonucleotide refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "extending", as used herein, refers to the extension of a primer by the addition of nucleotides using a polymerase. If a primer that is annealed to a nucleic acid is extended, the nucleic acid acts as a template for the extension reaction.

The term "circularizing", as used herein, refers to the ligation of one or more linear molecules to make a strand that is in the form of a closed circle that has no free 3' or 5' ends.

The term "unique sequence", as used herein, refers to nucleotide sequences that are different from one another, or their complements. For example, a first unique sequence has a different nucleotide sequence than a second unique sequence or its complement. Unless otherwise indicated, a unique sequence is only present in one polynucleotide in a sample.

The term "do not hybridize to each other", as used herein in the context of nucleic acids that do not hybridize to each other, refers to sequences that have been designed so that they do not anneal to one another under stringent conditions. Examples of such sequences are called "sequence tokens" in certain publications, are described in, e.g., US20070259357 and Brenner et al (Proc. Natl. Acad. Sci. 1992 89:5381-3), which are incorporated by reference herein.

The term "immediately adjacent", in the context of two nucleotides that are immediately adjacent to one another, means that there are no intervening nucleotides between two nucleotides. Nucleotides that are immediately adjacent to one another can be ligated to one another.

The term "similar to one another" in the context of a polynucleotide or polypeptide, means sequences that are at least 70% identical, at least 80% identical, at least 90% identical, or at least 95% identical, to one another.

The term "single stranded" refers to a nucleic acid strand that is present in a composition in single stranded form, not in double stranded form. In certain cases, a single stranded polynucleotide may be present in a composition in the absence of any complementary polynucleotide. In other cases, e.g., in cases in which a double stranded nucleic acid has been denatured, but not renatured, a single stranded polynucleotide may be present in a composition that also contains a complementary polynucleotide. However, in these cases, the polynucleotides are not base paired with one another.

The term "the same", in the context of two or more sequences that are the same, refers to two or more nucleic acids that have the same sequence of nucleotides. In other words, if all the polynucleotides of a population have the same sequence, then all of the polynucleotide molecules of the population have the same sequence of nucleotides.

The term "contacting" means to bring or put together. As such, a first item is contacted with a second item when the two items are brought or put together, e.g., by touching them to each other or combining them in the same solution. Thus, a "contacted sample" is a test chromosome onto which oligonucleotide probes have been hybridized.

The term "genotyping", as used herein, refers to any type of analysis of a nucleic acid sequence, and includes sequencing, polymorphism (e.g., SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of a oligonucleotide. Barcode sequences may vary widely in size and composition; the following references provide guidance for selecting sets of barcode sequences appropriate for particular embodiments: Brenner, U.S. Pat. No. 5,635, 400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population. The term "variable" means that the sequences varies between the different molecules of the population, and there may be duplicates of any particular sequence.

The term "reference genome" as used herein refers to a genome to which results obtained from a test genome can be compared. In certain cases, the region under study may be of known nucleotide sequence in a reference gene, e.g. the sequence may have been deposited at NCBI's Genbank database or other database, for example. In many embodiments, the test and reference genomes are genomes from the same (e.g., mammalian) species.

The term "chromosomal rearrangement," as used herein, refers to an event where one or more parts of a chromosome are rearranged within a single chromosome or between chromosomes. In certain cases, a chromosomal rearrangement may reflect an abnormality in chromosome structure. A chromosomal rearrangement may be an inversion, a deletion, an insertion or a translocation, for example.

The term "breakpoint", in the context of a chromosomal rearrangement, refers to a junction created by a chromosomal rearrangement. For example, if there is a rearrangement between chromosome 1 and chromosome 2, the breakpoint of the rearrangement is defined by the junction of the sequence from chromosome 1 and the sequence from chromosome 2 in the rearranged chromosome.

The following description explains the formulas used in this disclosure. Certain polynucleotides described herein may be referred by a formula (e.g., "$V_1$-B-$V_2$"). Such formulas follow the established convention in that they describe a polynucleotide that is oriented in the 5' to 3' direction. The components of the formula, e.g., "$V_1$", "B" and "$V_2$" refer to separately definable sequences of nucleotides within a polynucleotide, where the sequences are linked together covalently such that a polynucleotide described by a formula is a single molecule. The components of the formula may be immediately adjacent to one another or spaced from one another in the single molecule. By convention, the complement of a component shown in a formula will be indicated with a prime (') such that the complement of component "B" will be "B'". Moreover, unless otherwise indicated (e.g., if the formula is preceded with "5'-" such as in the case of "5'-$V_1$-B-$V_2$" or if the formula is followed by a "3'-" such as in the case of "$V_1$-B-$V_2$-3'", a polynucleotide defined by a formula may have additional sequence at its 3' end, its 5' end or both the 3' and 5' ends. In the context of a formula, the term nucleic acid sequence refers to the sequence of nucleotides of a component of the formula. For example, the phrase "nucleic acid sequence B" refers to the sequence of nucleotides of component B.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Methods

Certain embodiments of the method described herein make use of a "halo probe", where, in the context of this disclosure, such a probe is made up of an oligonucleotide of the formula $V_1$-B-$V_2$ and one or more second oligonucleotides that hybridize to region B. For reference purposes, two embodiments of a halo probe, 2 and 16 are shown in FIG. 1. As illustrated in FIG. 1, both embodiments of halo probe 2 and 16 comprise: a first oligonucleotide 4 comprising flanking sequences 8 and 10 that hybridize to different regions in a fragment target DNA and a central sequence 12. Flanking sequence 8 corresponds to the region referred to as "$V_1$" herein, flanking sequence 10 corresponds to the region referred to as "$V_2$" herein, and central sequence 12 corresponds to the region referred to as "B" herein. As shown, a halo probe further contains one or more second oligonucleotides that are complementary to central sequence 12 of the first oligonucleotide. In the context of this disclosure, these oligonucleotides will be referred to as one or more second oligonucleotides that hybridize to nucleic acid sequence B. In embodiment 2 (shown in panel A) the one or more second oligonucleotides can be a single oligonucleotide 14. In embodiment 16 (shown in panel B) the one or more second oligonucleotides can be two oligonucleotides 14a and 14b, which each contain a region that hybridizes to the first oligonucleotide, and a tail that does not hybridize to the first oligonucleotide. In certain embodiments, the one or more second oligonucleotides can provide amplification and/or sequencing primer binding sites, and, optionally, a molecular barcode sequence. These sequences may be present in the tails of oligonucleotides 14a and 14b if halo probe 16 is used. Either of the halo probes shown in FIG. 1 may be used in the methods described below. Solely for convenience in explaining the method, the figures illustrate methods that use the first embodiment of a halo probe shown in panel A of FIG. 1. Those methods can be readily adapted to the halo probe shown in panel B of FIG. 1.

The lengths of the various regions of a halo probe may vary greatly depending upon the desired application and how much freight (i.e., how many primer binding sites, barcodes, etc.) are carried by the one or more second oligonucleotides. In certain embodiments, the double stranded region of the halo probe may be of 20 to 100 base pairs (e.g., 30 bp to 60 bp) in length, and the sequences of the flanking regions 8 and 10 (specifically hybridize to a target sequence in a genome) may be of 10 to 100 bases (e.g., 12-50 bases) in length. As should be readily apparent, the nucleotide sequence of the double stranded region of the halo probe should be designed to that it does not hybridize to the genome under study.

Figure 2:
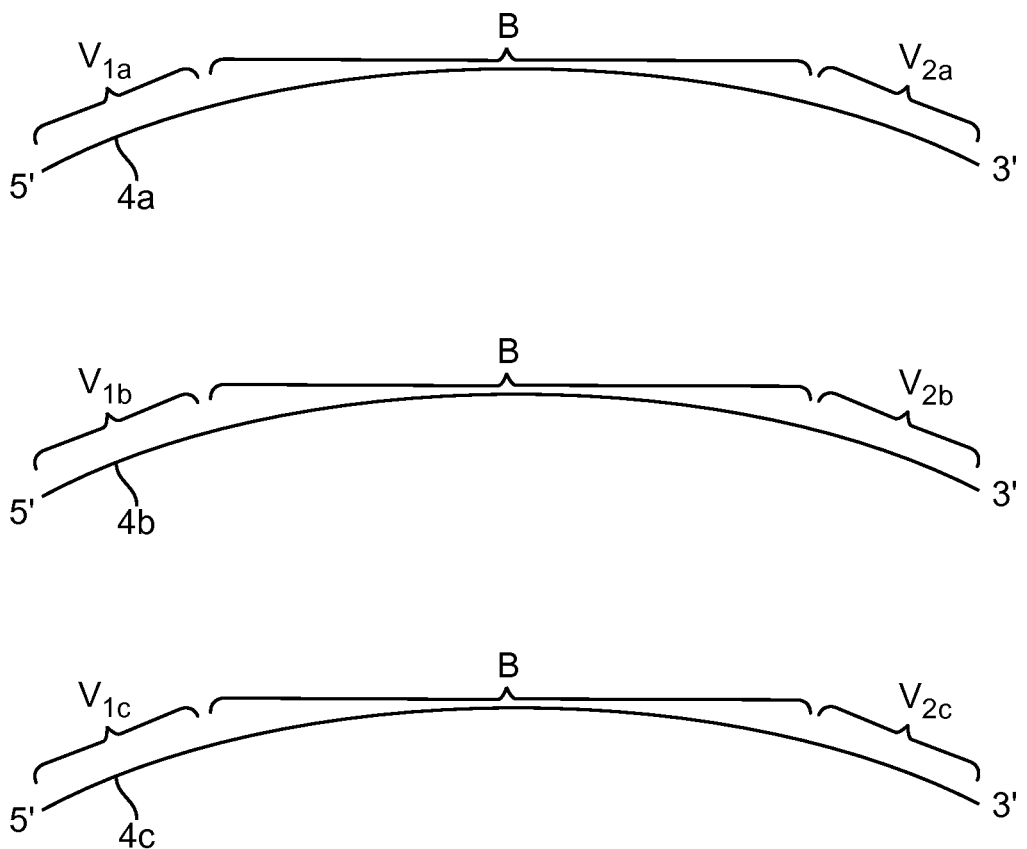

One embodiment of the method uses a population a single stranded oligonucleotides of the formula $V_1$-B-$V_2$ and one or more second oligonucleotides, where (i) the nucleic acid sequence B is the same for each of the first oligonucleotides; (ii) the nucleic acid sequence $V_1$ is variable; (iii) the nucleic acid sequence $V_2$ is variable; (iv) within each first oligonucleotide, the $V_1$ and $V_2$ sequences hybridize to unique sites that are at least 10 kb apart in a reference genome; and (v) the one or more secondary oligonucleotides hybridize to nucleic acid sequence B. B does not hybridize to the reference genome. FIG. 2 illustrates a population containing three exemplary first oligonucleotides 4a, 4b and 4c. As shown in FIG. 2, the nucleic acid sequence B is the same for each of the first oligonucleotide and hybridizes with the one or more second oligonucleotides (not shown). The sequences of $V_1$ and $V_2$ vary independently from one another. In the molecules shown, the 5' ends of the first oligonucleotides 4a, 4b and 4c have different sequences $V_{1a}$, $V_{1b}$ and $V_{1c}$ respectively and the 3' ends of the first oligonucleotides 4a, 4b and 4c have different sequences $V_{2a}$, $V_{2b}$ and $V_{2c}$, respectively. Consistent with FIG. 1, the one or more second oligonucleotides used in the method may be: a) single oligonucleotides that hybridize to the nucleic acid sequence B of the first oligonucleotides; or two oligonucleotides, each comprising a first region that hybridizes to the nucleic acid sequence B of the first oligonucleotides, and a second region that provides a binding site for an amplification primer.

Illustrated by example, in molecule 4a, sequences $V_{1a}$ and $V_{2a}$ bind to sites in a reference genome that are at least 10 kb from one another, in molecule 4b, sequences $V_{1b}$ and $V_{2b}$ bind to sites in the reference genome that are at least 10 kb from one another, and in molecule 4c, sequences $V_{1c}$ and $V_{2c}$ bind to sites in the reference genome that are at least 10 kb from one another. Within each molecule, $V_1$ and $V_2$ hybridize to sites in a reference genome that are separated by a distance that makes it difficult or impossible to routinely obtain a product by polymerase chain reaction. In certain cases, the sites to which $V_1$ and $V_2$ hybridize are at least 10 kb apart in a reference genome although, in certain embodiments, this distance may be shorter, e.g., at least 2 kb or at least 5 kb. In certain cases, within each first oligonucleotide, the sequences to which $V_1$ and $V_2$ hybridize may be at least 20 kb, at least 50 kb, at least 100 kb, or at least 500 kb apart in the reference chromosome. In particular embodiments, the sequences to which $V_1$ and $V_2$ hybridize may be on different chromosome arms in the reference genome. Specifically, in any one first oligonucleotide molecule, the $V_1$ and $V_2$ sequences may hybridize to the long and short arm of the same chromosome, respectively, or vice versa. In other embodiments, in any one first oligonucleotide molecule, the $V_1$ and $V_2$ sequences may hybridize to different chromosomes (e.g., the $V_1$ sequence may hybridize to chromosome 1 and the $V_2$ sequence may hybridize to chromosome 2). In certain cases, the population of first oligonucleotides may be designed such that the $V_1$ sequences of the population hybridize to sites that are all in one strand in a first region in a reference genome (e.g., at sites that are distributed throughout, e.g., tiled through, a 50 kb or 100 kb region), and the $V_2$ sequences of the population hybridize to sites that are all in one strand in a second region in the reference genome (e.g., at sites that are distributed throughout, e.g., tiled through, a 50 kb or 100 kb region), where the first and second regions are known to rearrange with one another in other genomes.

In these embodiments, the $V_1$ and $V_2$ sequences of the first oligonucleotides can be designed so that they hybridize to the same strand in a rearranged genome. Finally, the $V_1$ and $V_2$ sequences may be designed so that they hybridize immediately next to restriction sites in the reference genome. In these embodiments, a fragment produced by digestion of the genome with a restriction enzyme, a first oligonucleotide and a second oligonucleotide hybridize to produce a complex in which at least one of the ends of at least one second oligonucleotide is ligatably adjacent to one of the ends of the fragment, as described in U.S. Pat. No. 7,883,849 and Dahl et al. (Nucl. Acids. Res. 2005 33: e71), which are incorporated by reference herein. Sequences $V_1$, B and $V_2$ are each at least 15 nucleotides in length. In some embodiments, sequences $V_1$, B and $V_2$ may independently be at least 18 nucleotides in length, at least 20 nucleotides in length, at least 25 nucleotides in length, at least 30 nucleotides in length, up to 50 nucleotides in length or more.

The size of the population of first oligonucleotides may vary greatly depending on how the method is being performed. In some embodiments, the population may contain at least 10, at least 50, at least 100, at least 200, at least 500, or at least 1,000 and up to 1,0000 or more first oligonucleotides. Further, the method may be performed using multiple different populations of first oligonucleotides. For example, if a first population of first oligonucleotides is designed to hybridize to regions in a reference genome that are known to rearrange with one another in other genomes, the method may be done using a second population of first oligonucleotides that designed to hybridize to different regions in a reference genome that are known to rearrange with one another in other genomes. A method may be done with at least 1, at least 2, at least 5, at least 10 or at least 100 or more different populations of first oligonucleotides.

Figure 3:
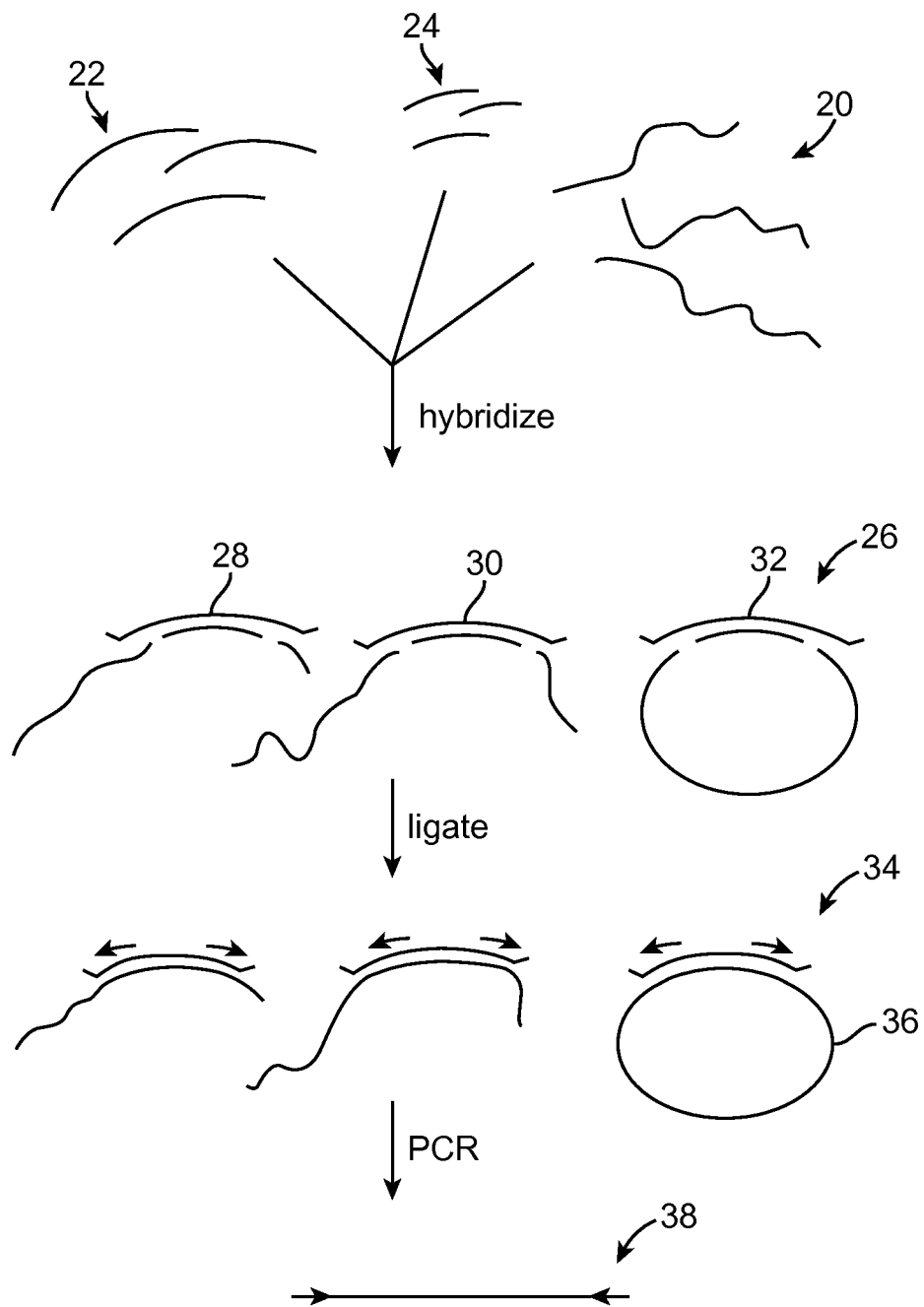

As shown in FIG. 3, certain embodiments of the method may comprise (a) hybridizing fragmented genomic DNA 20 from a test genome with the population of first oligonucleotides 22 in the presence of one or more second oligonucleotides 24 to produce a hybridization product 26. As shown, the hybridization product contains a number of complexes, e.g., 28, 30 and 32. As shown, many of the first oligonucleotides, e.g., those in complexes 28 and 30, are hybridized to two distinct genomic fragments, which would be expected because, within each first oligonucleotide molecule, the $V_1$ and $V_2$ sequences hybridized to sites in a genome that are distanced by at least 10 kb. In certain cases, the test genome may have a chromosomal rearrangement relative to the reference genome that effectively moves a $V_1$-complemenary sequence to a site that is both proximal to and on the same strand as $V_2$-complemenary sequence. In these cases, if a first oligonucleotide contains $V_1$ and $V_2$ sequences that are complementary to the sequences moved into proximity by the rearrangement, complex 32 that comprises a single genomic fragment that is hybridized to both ends of a first oligonucleotide is produced. As described above, in certain embodiments the first oligonucleotides are designed so that the $V_1$ and $V_2$ sequences are next to cleavage sites for a restriction enzyme in the reference genome. In these embodiments, the ends of the fragment in complex 32 may be ligatably adjacent to the ends of the second oligonucleotide of the complex. In other embodiments, the ends of the fragment can be trimmed back using, e.g., an exonuclease and/or flap endonuclease to provide a complex in which the ends of the fragment are ligatably adjacent to the ends of the second oligonucleotide in the complex.

After hybridization, hybridization products 26 are contacted with a ligase in order to join the ends of the fragmented genomic DNA to the one or more second oligonucleotides to produce ligation products 34. As shown, in complexes that contain a single fragment that is hybridized to both ends of a first oligonucleotide, both ends of the fragment ligate to the one or more second oligonucleotides. In the embodiment shown (which employs a halo probe shown in panel A of FIG. 1), ligation produces circular nucleic acid molecule 36. In embodiments that employ the halo probe illustrated in panel B of FIG. 1, the genomic fragment becomes ligated two different oligonucleotides (e.g., 14a and 14b, as illustrated in panel B of FIG. 1), which effectively adds an adaptor to both ends of a genomic fragment.

After ligation, the ligation products 34 are subjected to polymerase chain reaction conditions using amplification primers that hybridize to sites that are provided by the one or more second oligonucleotides, where as noted above, if an oligonucleotide provides a binding site for a primer, then the primer may hybridize to that oligonucleotide or its complement. Exemplary sites of the amplification primers are indicated using arrows in FIG. 3. Equivalent binding sites can be provided by the alternative second oligonucleotides illustrated in panel B of FIG. 1. Production of product 28 by the amplification step indicates that the test genome contains a chromosomal rearrangement relative to the reference genome. If there is no rearrangement that brings a $V_1$-complemenary sequence to a site that is both proximal to and on the same strand as $V_2$-complemenary sequence, then no amplification product will be obtained.

In certain embodiments, the method may further comprise sequencing the amplification product 38. This sequencing can done using primers that hybridize to the complementary strand of the one or more second oligonucleotides. This method may be analyzed to identify the breakpoint for the chromosomal rearrangement.

As would be apparent, in certain embodiments, the sequences added by the one or more second oligonucleotides may contain sequences that are compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The sequences may be present in the one or more second oligonucleotides (either in their tails or in the sequence that hybridizes to the first oligonucleotide). In certain cases, the one of more second oligonucleotides may contain two sets of primer binding sites, one for amplifying the circular DNA by inverse PCR, and the other for sequencing the resultant product. The one or more second oligonucleotides may also contain a molecular barcode, positioned downstream of the amplification and sequencing primer binding sites, that can be used to identify from which sample a sequence is derived, or to count how many different starting molecules have been sequenced.

In other embodiments, the amplicon may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. patent application publications US2006003171 and US20090029477.

In particular embodiments, the fragmented genomic DNA may be made by digesting genomic DNA using a restriction enzyme, e.g., one or more restriction enzymes that have a four, five or six base pair recognition site. Alternatively, the genomic DNA may be produced from genomic DNA using chemical, physical or transposase-catalyzed fragmentation methods, see, e.g., Adey et al (Genome Biology 2010, 11:R119). For example, the physical fragmentation methods may include sonication, nebulization, or shearing of genomic DNA. In certain embodiments, prior to performing the method, the genomic DNA may be fragmented to an average size in the range of 100 bp to 10 kb, e.g., 200 bp to 1 kb.

The method described above may be used to analyze a genome from virtually any organism, e.g., plants, animals (e.g., reptiles, mammals such as humans and mice, insects, worms, fish, etc.), tissue samples, bacteria, fungi (e.g., yeast), phage, viruses, cadaveric tissue, archaeological/ancient samples, etc. In certain embodiments, the initial DNA used in the method may be derived from a mammal, where in certain embodiments the mammal is a human. In one embodiment, the test genome is suspected of containing a chromosomal rearrangement.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. In addition, the reaction may be multiplex such that a plurality of different target loci (e.g., 10 to 1000) are targeted in a single reaction.

Compositions

A composition comprising a population of first oligonucleotides of the formula $V_1$-B-$V_2$ is provided. In certain embodiments, (i) the nucleic acid sequence B is the same for each of the first oligonucleotides and is at least 15 nucleotides in length, (ii) the nucleic acid sequence $V_1$ is variable, (iii) the nucleic acid sequence $V_2$ is variable, and (iv) within each first oligonucleotide, the $V_1$ and $V_2$ sequences hybridize to sites that are at least 10 kb apart in a reference genome. The composition may further comprise one or more second oligonucleotides that that hybridize to the nucleic acid sequence B of the first oligonucleotides and, optionally, fragmented genomic DNA. A more detailed description of the components that may be present in this composition as well as other components that may be present in the composition are described in the methods section set forth above.

Kits

Also provided by this disclosure is a kit for practicing the subject method, as described above. A subject kit may contain at least: a) a population of the first oligonucleotides of the formula $V_1$-B-$V_2$, wherein (i) the nucleic acid sequence B is the same for of the first oligonucleotides and is at least 15 nucleotides in length, (ii) the nucleic acid sequence $V_1$ is variable, (iii) the nucleic acid sequence $V_2$ is variable, and (iv) within each first oligonucleotide, the $V_1$ and $V_2$ sequences hybridize to sites that are at least 10 kb apart in a reference genome; and b) one or more second oligonucleotides that hybridize to the nucleic acid sequence B of the first oligonucleotides. The kit may further comprise amplification primers that hybridize to sites provided by the one or more second oligonucleotides. In addition, the kit may also contain reagents for performing primer extension (e.g., polymerase, nucleotides and buffer, etc.), and other enzymes and/or reagents for performing the method, e.g., a ligase, etc. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject method finds use in a variety of applications, where such applications generally include genomic DNA analysis applications in which the presence of a particular chromosomal rearrangement in a given sample is to be detected. The subject methods may also be used to finely map chromosomal breakpoints, and other aberrations, such as micro-inversions, deletions and translocations in certain cases without a priori knowledge of their location. The subject methods find use in a variety of diagnostic and research purposes since chromosomal inversions and translocations play an important role in conditions relevant to human diseases and genomic evolution of many organisms.

In particular, the above-described methods may be employed to diagnose, or investigate various types of genetic abnormalities, cancer or other mammalian diseases, including but not limited to, leukemia; breast carcinoma; prostate cancer; Alzheimer's disease; Parkinson's disease; epilepsy; amyotrophic lateral sclerosis; multiple sclerosis; stroke; autism; Cri du chat (truncation on the short arm on chromosome 5), 1p36 deletion syndrome (loss of part of the short arm of chromosome 1), Angelman syndrome (loss of part of the long arm of chromosome 15); Prader-Willi syndrome (loss of part of the short arm of chromosome 15); acute lymphoblastic leukemia and more specifically, chronic myelogenous leukemia (translocation between chromosomes 9 and 22); Velocardiofacial syndrome (loss of part of the long arm of chromosome 22); Turner syndrome (single X chromosome); Klinefelter syndrome (an extra X chromosome); Edwards syndrome (trisomy of chromosome 18); Down syndrome (trisomy of chromosome 21); Patau syndrome (trisomy of chromosome 13); and trisomies 8, 9 and 16, which generally do not survive to birth.

The disease may be genetically inherited (germline mutation) or sporadic (somatic mutation). Many exemplary chromosomal rearrangements discussed herein are associated with and are thought to be a factor in producing these disorders. Knowing the type and the location of the chromosomal rearrangement may greatly aid the diagnosis, prognosis, and understanding of various mammalian diseases.

Certain of the above-described methods can also be used to detect diseased cells more easily than standard cytogenetic methods, which require dividing cells and require labor and time-intensive manual preparation and analysis of the slides by a technologist.

The above-described methods can also be used to compare the genomes of two biological species in order to deduce evolutionary relationships.

Genomic DNA may be isolated from a variety of sources, including tissue culture cells and mammalian subjects, e.g., human, primate, mouse or rat subjects. For example, chromosomes may be analyzed from less than five milliliters (mL) of peripheral blood. White blood cells contain chromosomes while red blood cells do not. Blood may be collected and combined with an anti-clotting agent such as sodium heparin. Genomic DNA may also be analyzed from amniotic fluid, which contains fetal cells. Such cells can be grown in tissue culture so that dividing cells are available for chromosomal analysis within 5-10 days. Genomic DNA may also be analyzed from bone marrow, which is useful for diagnosis of leukemia or other bone marrow cancers. Genomic DNA may also be analyzed from solid tissue samples. A skin or other tissue biopsy in the range of about 2-3 mm may be obtained aseptically and transferred to a sterile vial containing sterile saline or tissue transport media to provide material for chromosome analysis. Fetal tissue obtained after a miscarriage can also be used for chromosome analysis, such as from the fetal side of the placenta, the periosteum overlying the sternum or fascia above the inguinal ligament, or from chorionic villi. Fetal tissue can also be collected from multiple sites such as the kidneys, thymus, lungs, diaphragm, muscles, tendons, and gonads. An amniocentesis may also be performed.

In addition to the above, the instant methods may also be performed on bone marrow smears, blood smears, paraffin embedded tissue preparations, enzymatically dissociated tissue samples, uncultured bone marrow, uncultured amniocytes and cytospin preparations, for example.

Examples

Figure 4:
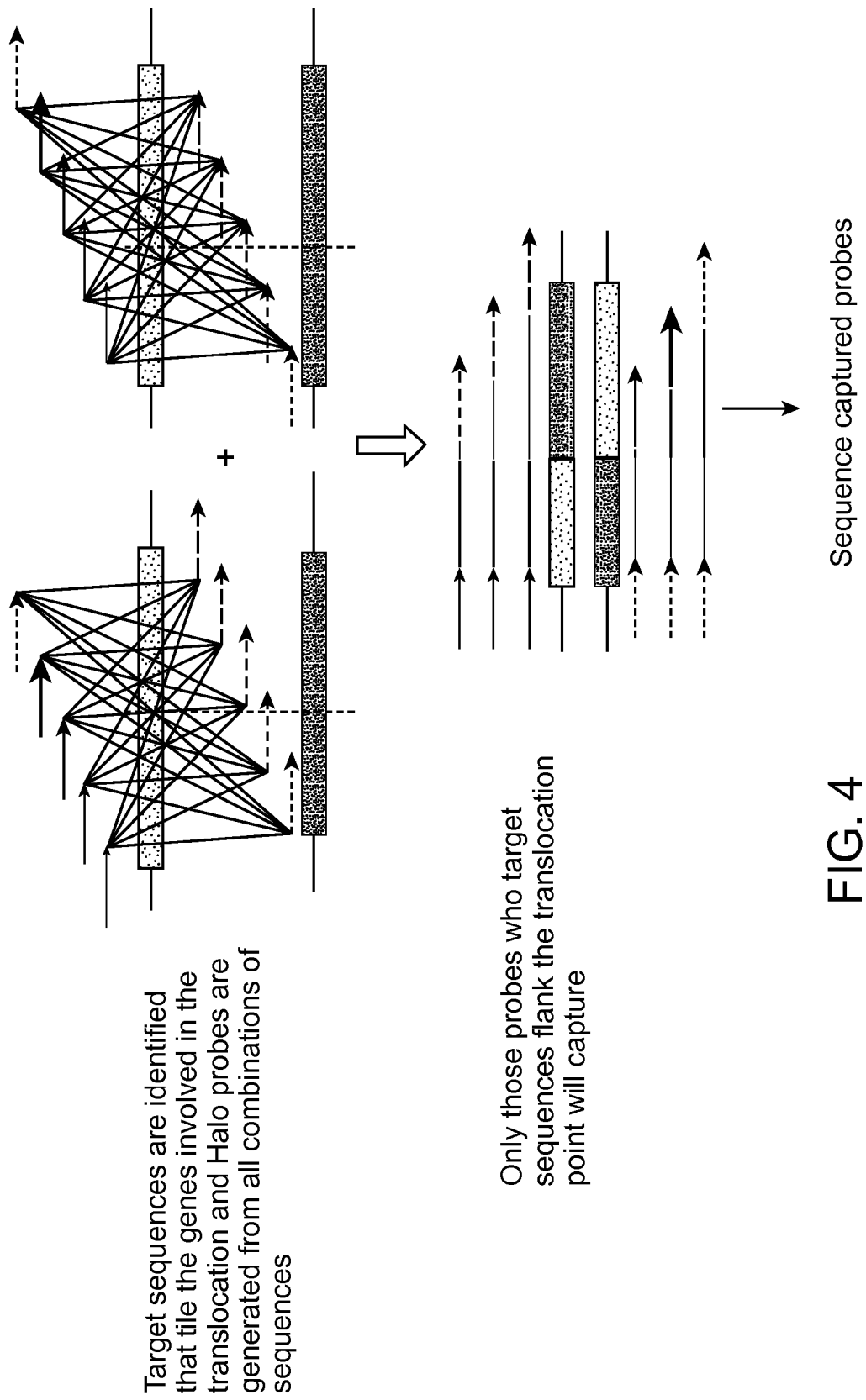

In this example, the method described above is applied to detect gene fusions created by the translocation and/or inversion of chromosomes or chromosome segments. In this example, a halo probe is use to capture a specific DNA sequence from a complex pool of sequences. This captured sequence is subsequently amplified and sequenced using a next-generation sequencing platform. As described above, a halo probe consists of two gene specific sequences that are complementary to the 5' and 3' ends of the targeted sequence. The halo method is able to detect sequences in which the two Halo probe sequences are separated by <~400 bp of intervening sequence. For the detection of translocations, the two sequences targeted by the halo probe are complementary to the partner genes that become fused by the translocation. In samples without the translocation, the two sequences would be on different chromosomes, or if on the same chromosome, would be separated by more than 400 bp and therefore no sequences would be captured. The translocation would bring the two Halo probe sequences to within 400 bp of each other, allowing capture of the sequence. An example of this is shown in FIG. 4. Not only does this method detect translocations but, because the captured DNA is sequenced, the precise fusion point can be determined.

Many translocations involve multiple break/fusion points so to enable capturing the fusion irrespective of where in occurs within the target gene, thus, in one embodiment, the halo probes are designed to tile the gene at ~50 bp intervals to ensure that the fusion point would be bracketed by halo sequences <400 bp apart.

Figure 5:
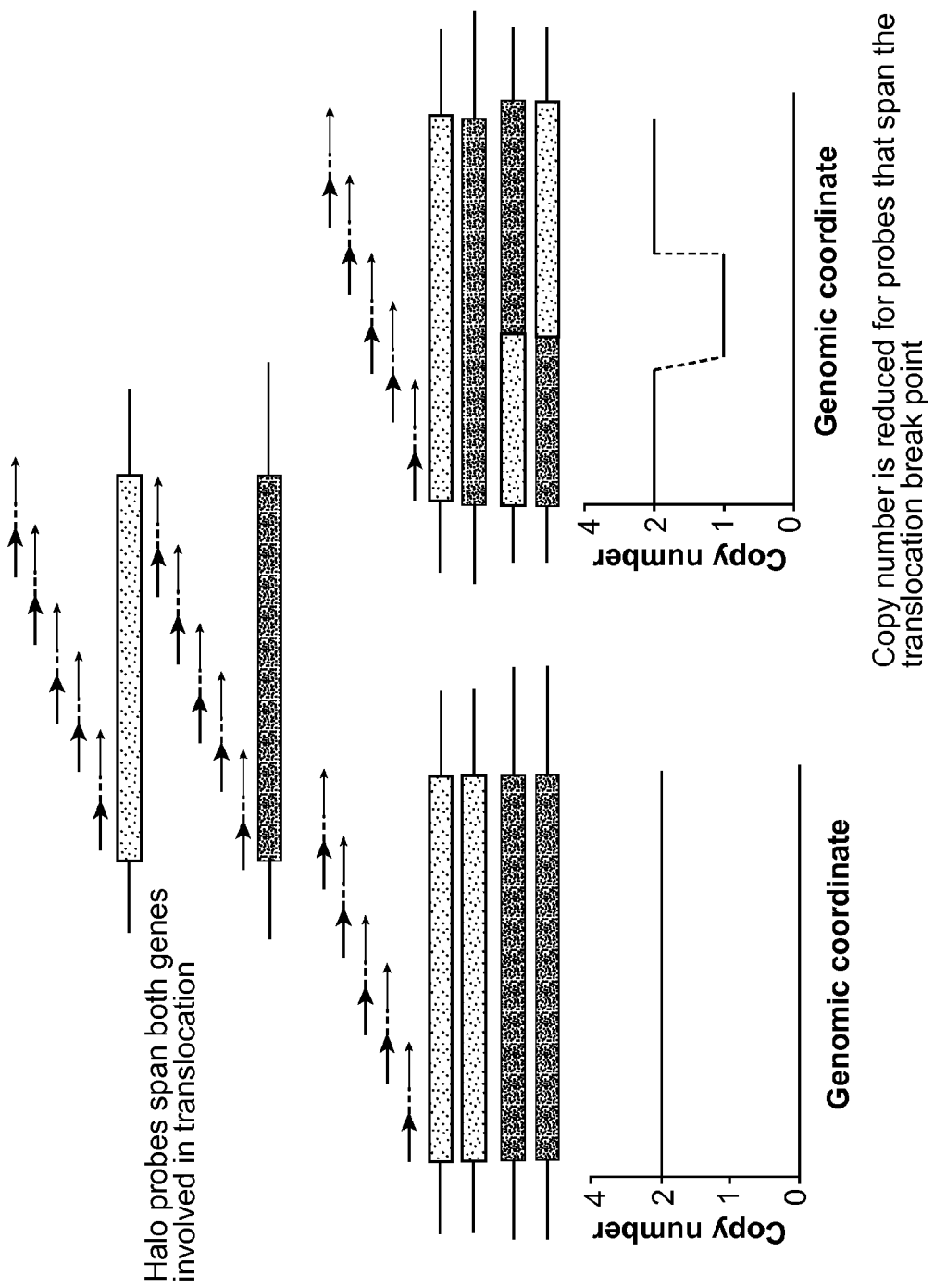

The production of fused sequences during a translocation event means that the number of intact (non-translocated) copies of a sequence will be reduced by 1. This reduction can potentially be measured using halo probes designed against the two genes involved in the translocation. In this case, the probe that flanks the translocation point for each of the genes will show a reduction in copy number relative to the other probes in the gene (see FIG. 5).

The invention claimed is:
1. A method of sample analysis, comprising:
  (a) hybridizing fragmented genomic DNA from a test genome with a population of first oligonucleotides of the formula $V_1$-B-$V_2$ in the presence of one or more second oligonucleotides; wherein;
    (i) the nucleic acid sequence B is the same for each of said first oligonucleotides and is at least 15 nucleotides in length;
    (ii) the nucleic acid sequence $V_1$ is variable;
    (iii) the nucleic acid sequence $V_2$ is variable;
    (iv) within each first oligonucleotide, the $V_1$ and $V_2$ sequences hybridize to sites that are at least 10 kb apart in a reference genome; and
    (v) said one or more second oligonucleotides hybridize to nucleic acid sequence B;
  (b) contacting the product of (a) with ligase to join the ends of said fragmented genomic DNA that are hybridized to $V_1$ and $V_2$ to the one or more second oligonucleotides; and
  (c) subjecting the product of (b) to polymerase chain reaction conditions using amplification primers that hybridize to sites that are provided by said one or more second oligonucleotides,
  wherein production of a product by step (c) indicates that said test genome contains a chromosomal rearrangement relative to said reference genome.
2. The method of claim 1, further comprising sequencing the product of (c).
3. The method of claim 2, further comprising analyzing the sequence to identify the breakpoint for said chromosomal rearrangement.
4. The method of claim 1, wherein, within each first oligonucleotide, the $V_1$ and $V_2$ sequences hybridize to sites that are on different chromosome arms in the reference genome.
5. The method of claim 1, wherein, within each first oligonucleotide, the $V_1$ and $V_2$ sequences hybridize to sites that are on different chromosomes in the reference genome.
6. The method of claim 1, wherein said test and reference genomes are mammalian genomes from the same species.

7. The method of claim 1, wherein said fragmented genomic DNA is made by digesting genomic DNA using a restriction enzyme.

8. The method of claim 1, wherein said one or more second oligonucleotides are single oligonucleotides that hybridize to the nucleic acid sequence B of said first oligonucleotides.

9. The method of claim 1, wherein said one or more second oligonucleotides are two oligonucleotides, each comprising a first region that hybridizes to the nucleic acid sequence B of said first oligonucleotides, and a second region that provides a binding site for an amplification primer of (c).

10. The method of claim 1, wherein $V_1$ and $V_2$ are each at least 15 bases in length.

11. The method of claim 1, wherein said the $V_1$ sequences are tiled across a first region in said reference genome and the $V_2$ sequences are tiled across a second region in said reference genome.

12. The method of claim 1, wherein said test genome is suspected of containing a chromosomal rearrangement.

13. The method of claim 1, wherein said fragmented genomic DNA are polynucleotides having a length up to 10,000 bases.

14. The method of claim 1, wherein said fragmented genomic DNA has an average size in the range of 100 bp to 10 kb.

15. The method of claim 1, wherein said fragmented genomic DNA has an average size in the range of 200 bp to 1 kb.

16. The method of claim 1, wherein, within each first oligonucleotide, the $V_1$ and $V_2$ sequences hybridize to sites that are on the same chromosome.

* * * * *